(12) United States Patent
Oral et al.

(10) Patent No.: US 9,005,194 B2
(45) Date of Patent: *Apr. 14, 2015

(54) ATRIAL ABLATION CATHETER ADAPTED FOR TREATMENT OF SEPTAL WALL ARRHYTHMOGENIC FOCI AND METHOD OF USE

(75) Inventors: Hakan Oral, Ann Arbor, MI (US); Randell L. Werneth, San Diego, CA (US); Thomas M. Castellano, Temecula, CA (US); Christopher G. Kunis, San Diego, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1615 days.

This patent is subject to a terminal disclaimer.

(21) Appl. No.: 12/176,115

(22) Filed: Jul. 18, 2008

(65) Prior Publication Data
US 2008/0275443 A1 Nov. 6, 2008

Related U.S. Application Data

(63) Continuation of application No. 10/997,713, filed on Nov. 24, 2004, now Pat. No. 7,468,062.

(51) Int. Cl.
*A61B 18/14* (2006.01)
*A61B 18/00* (2006.01)

(52) U.S. Cl.
CPC ..... *A61B 18/1492* (2013.01); *A61B 2018/0016* (2013.01); *A61B 2018/00214* (2013.01); *A61B 2018/00267* (2013.01); *A61B 2018/00351* (2013.01); *A61B 2018/1475* (2013.01)

(58) Field of Classification Search
USPC .................. 606/41, 45–50; 607/101, 102, 122
See application file for complete search history.

(56) References Cited

U.S. PATENT DOCUMENTS

| | | | |
|---|---|---|---|
| 3,516,412 A | 6/1970 | Ackerman |
| 3,951,136 A | 4/1976 | Wall |
| 4,017,903 A | 4/1977 | Chu |
| 4,112,952 A | 9/1978 | Thomas et al. |
| 4,411,266 A | 10/1983 | Cosman |
| 4,432,377 A | 2/1984 | Dickhudt |
| 4,660,571 A | 4/1987 | Hess et al. |
| 4,699,147 A | 10/1987 | Chilson et al. |
| 4,785,815 A | 11/1988 | Cohen |

(Continued)

FOREIGN PATENT DOCUMENTS

| | | |
|---|---|---|
| AU | 5200671AA | 10/2005 |
| CA | 2327322AA | 11/1999 |

(Continued)

OTHER PUBLICATIONS

Oral et al.; U.S. Appl. No. 11/932,378 entitled "Ablation catheters and methods for their use," filed Oct. 31, 2007.

(Continued)

*Primary Examiner* — Michael Peffley
(74) *Attorney, Agent, or Firm* — Christopher & Weisberg, P.A.

(57) ABSTRACT

An atrial ablation catheter with an electrode array particularly adapted to locate and ablate foci of arrhythmia which are required for sustained atrial fibrillation is provided. The array is easily deployed and retracted from the catheter, and presents a proximally oriented electrode array that can be pulled against the septal wall of the left atrium to engage the septal wall.

34 Claims, 7 Drawing Sheets

(56) References Cited

U.S. PATENT DOCUMENTS

| | | |
|---|---|---|
| 4,860,769 A | 8/1989 | Fogarty et al. |
| 4,869,248 A | 9/1989 | Narula |
| 4,882,777 A | 11/1989 | Narula |
| 4,896,671 A | 1/1990 | Cunningham et al. |
| 4,907,589 A | 3/1990 | Cosman |
| 4,920,980 A | 5/1990 | Jackowski |
| 4,940,064 A | 7/1990 | Desai |
| 4,966,597 A | 10/1990 | Cosman |
| 5,010,894 A | 4/1991 | Edhag |
| 5,016,808 A | 5/1991 | Heil, Jr. et al. |
| 5,083,565 A | 1/1992 | Parins |
| 5,100,423 A | 3/1992 | Fearnot |
| 5,156,151 A | 10/1992 | Imran |
| 5,184,621 A | 2/1993 | Vogel et al. |
| 5,215,103 A | 6/1993 | Desai |
| 5,228,442 A | 7/1993 | Imran |
| 5,230,349 A | 7/1993 | Langberg |
| 5,231,987 A | 8/1993 | Robson |
| 5,231,995 A | 8/1993 | Desai |
| 5,234,004 A | 8/1993 | Hascoet et al. |
| 5,239,999 A | 8/1993 | Imran |
| 5,255,679 A * | 10/1993 | Imran ........................ 600/375 |
| 5,279,299 A | 1/1994 | Imran |
| 5,281,213 A | 1/1994 | Milder et al. |
| 5,281,218 A | 1/1994 | Imran |
| 5,309,910 A | 5/1994 | Edwards et al. |
| 5,313,943 A | 5/1994 | Houser et al. |
| 5,318,525 A | 6/1994 | West et al. |
| 5,324,284 A | 6/1994 | Imran |
| 5,327,889 A | 7/1994 | Imran |
| 5,330,466 A | 7/1994 | Imran |
| 5,334,193 A | 8/1994 | Nardella |
| 5,342,295 A | 8/1994 | Imran |
| 5,342,357 A | 8/1994 | Nardella |
| 5,345,936 A | 9/1994 | Pomeranz et al. |
| 5,348,554 A | 9/1994 | Imran et al. |
| D351,652 S | 10/1994 | Thompson et al. |
| 5,364,352 A | 11/1994 | Cimino et al. |
| 5,365,926 A | 11/1994 | Desai |
| 5,370,644 A | 12/1994 | Langberg |
| 5,383,917 A | 1/1995 | Desai et al. |
| 5,391,147 A | 2/1995 | Imran et al. |
| 5,397,304 A | 3/1995 | Truckai |
| 5,397,339 A | 3/1995 | Desai |
| 5,400,783 A | 3/1995 | Pomeranz et al. |
| 5,404,638 A | 4/1995 | Imran |
| 5,406,946 A | 4/1995 | Imran |
| 5,411,025 A | 5/1995 | Webster, Jr. |
| 5,423,808 A | 6/1995 | Edwards et al. |
| 5,423,811 A | 6/1995 | Imran et al. |
| 5,433,198 A | 7/1995 | Desai |
| 5,433,739 A | 7/1995 | Sluijter et al. |
| 5,445,148 A | 8/1995 | Jaraczewski et al. |
| 5,462,521 A | 10/1995 | Brucker et al. |
| 5,462,545 A | 10/1995 | Wang et al. |
| 5,465,717 A | 11/1995 | Imran et al. |
| 5,471,982 A | 12/1995 | Edwards et al. |
| 5,487,757 A | 1/1996 | Truckai et al. |
| 5,492,119 A | 2/1996 | Abrams |
| 5,500,011 A | 3/1996 | Desai |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,536,267 A | 7/1996 | Edwards et al. |
| 5,540,681 A | 7/1996 | Strul et al. |
| 5,545,161 A | 8/1996 | Imran |
| 5,545,193 A | 8/1996 | Fleischman et al. |
| 5,545,200 A | 8/1996 | West et al. |
| 5,558,073 A | 9/1996 | Pomeranz et al. |
| 5,573,533 A | 11/1996 | Strul |
| 5,575,766 A | 11/1996 | Swartz et al. |
| 5,575,810 A | 11/1996 | Swanson et al. |
| 5,578,007 A | 11/1996 | Imran |
| 5,582,609 A | 12/1996 | Swanson et al. |
| 5,584,830 A | 12/1996 | Ladd et al. |
| 5,588,432 A | 12/1996 | Crowley |
| 5,588,964 A | 12/1996 | Imran et al. |
| 5,595,183 A | 1/1997 | Swanson et al. |
| 5,596,995 A | 1/1997 | Sherman et al. |
| 5,598,848 A | 2/1997 | Swanson et al. |
| 5,601,088 A | 2/1997 | Swanson et al. |
| 5,606,974 A | 3/1997 | Castellano et al. |
| 5,607,462 A | 3/1997 | Imran |
| 5,620,481 A | 4/1997 | Desai et al. |
| 5,626,136 A | 5/1997 | Webster, Jr. |
| 5,630,425 A | 5/1997 | Panescu et al. |
| 5,630,837 A | 5/1997 | Crowley |
| 5,637,090 A | 6/1997 | McGee et al. |
| D381,076 S | 7/1997 | Thornton et al. |
| 5,645,064 A | 7/1997 | Littmann et al. |
| 5,645,082 A | 7/1997 | Sung et al. |
| 5,656,029 A | 8/1997 | Imran et al. |
| 5,657,755 A | 8/1997 | Desai |
| 5,658,278 A | 8/1997 | Imran et al. |
| 5,662,606 A | 9/1997 | Cimino et al. |
| 5,666,970 A | 9/1997 | Smith |
| 5,673,695 A | 10/1997 | McGee et al. |
| 5,680,860 A * | 10/1997 | Imran ........................ 600/374 |
| 5,681,280 A | 10/1997 | Rusk et al. |
| 5,682,885 A | 11/1997 | Littmann et al. |
| 5,685,322 A | 11/1997 | Sung et al. |
| 5,687,723 A | 11/1997 | Avitall |
| 5,693,078 A | 12/1997 | Desai et al. |
| 5,697,927 A | 12/1997 | Imran et al. |
| 5,697,928 A | 12/1997 | Walcott et al. |
| 5,699,796 A | 12/1997 | Littmann et al. |
| 5,702,438 A * | 12/1997 | Avitall ........................ 607/122 |
| 5,704,791 A | 1/1998 | Gillio |
| 5,706,809 A | 1/1998 | Littmann et al. |
| 5,711,298 A | 1/1998 | Littmann et al. |
| 5,716,389 A | 2/1998 | Walinsky et al. |
| 5,722,401 A | 3/1998 | Pietroski et al. |
| 5,722,975 A | 3/1998 | Edwards et al. |
| 5,724,985 A | 3/1998 | Snell et al. |
| 5,733,323 A | 3/1998 | Buck et al. |
| 5,735,280 A | 4/1998 | Sherman et al. |
| 5,741,320 A | 4/1998 | Thornton et al. |
| 5,766,152 A | 6/1998 | Morley et al. |
| 5,769,791 A | 6/1998 | Benaron et al. |
| 5,769,847 A | 6/1998 | Panescu et al. |
| 5,772,590 A | 6/1998 | Webster, Jr. |
| 5,775,327 A | 7/1998 | Randolph et al. |
| 5,782,239 A | 7/1998 | Webster, Jr. |
| 5,782,760 A | 7/1998 | Schaer |
| 5,782,828 A | 7/1998 | Chen et al. |
| 5,782,899 A | 7/1998 | Imran |
| 5,792,140 A | 8/1998 | Tu et al. |
| 5,800,482 A | 9/1998 | Pomeranz et al. |
| 5,810,740 A | 9/1998 | Paisner |
| 5,820,568 A | 10/1998 | Willis |
| 5,827,272 A | 10/1998 | Breining et al. |
| 5,837,001 A | 11/1998 | Mackey |
| 5,849,028 A | 12/1998 | Chen |
| 5,857,464 A | 1/1999 | Desai |
| 5,857,997 A | 1/1999 | Cimino et al. |
| 5,860,920 A | 1/1999 | McGee et al. |
| 5,863,291 A | 1/1999 | Schaer |
| 5,871,523 A | 2/1999 | Fleischman et al. |
| 5,873,865 A | 2/1999 | Horzewski et al. |
| 5,876,399 A | 3/1999 | Chia et al. |
| 5,881,732 A | 3/1999 | Sung et al. |
| 5,882,333 A | 3/1999 | Schaer et al. |
| 5,885,278 A | 3/1999 | Fleischman |
| 5,891,027 A | 4/1999 | Tu et al. |
| 5,891,135 A | 4/1999 | Jackson et al. |
| 5,891,137 A | 4/1999 | Chia et al. |
| 5,891,138 A | 4/1999 | Tu et al. |
| 5,893,847 A * | 4/1999 | Kordis ........................ 600/41 |
| 5,893,884 A | 4/1999 | Tu |
| 5,893,885 A | 4/1999 | Webster, Jr. |
| 5,895,355 A | 4/1999 | Schaer |
| 5,895,417 A | 4/1999 | Pomeranz et al. |
| 5,897,554 A | 4/1999 | Chia et al. |

(56) References Cited

U.S. PATENT DOCUMENTS

| | | |
|---|---|---|
| 5,904,680 A | 5/1999 | Kordis et al. |
| 5,906,605 A | 5/1999 | Coxum |
| 5,910,129 A | 6/1999 | Koblish et al. |
| 5,911,720 A | 6/1999 | Bourne et al. |
| 5,913,854 A | 6/1999 | Maguire et al. |
| 5,916,214 A | 6/1999 | Cosio et al. |
| 5,928,191 A | 7/1999 | Houser et al. |
| 5,931,835 A | 8/1999 | Mackey |
| 5,935,063 A | 8/1999 | Nguyen |
| 5,938,694 A | 8/1999 | Jaraczewski et al. |
| 5,941,845 A | 8/1999 | Tu et al. |
| 5,951,471 A | 9/1999 | de la Rama et al. |
| 5,954,719 A | 9/1999 | Chen et al. |
| 5,957,842 A | 9/1999 | Littmann et al. |
| 5,960,796 A | 10/1999 | Sung et al. |
| 5,967,978 A | 10/1999 | Littmann et al. |
| 5,968,040 A | 10/1999 | Swanson et al. |
| 5,971,980 A | 10/1999 | Sherman |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,004,269 A | 12/1999 | Crowley et al. |
| 6,014,581 A | 1/2000 | Whayne et al. |
| 6,021,340 A | 2/2000 | Randolph et al. |
| 6,023,638 A | 2/2000 | Swanson |
| 6,029,091 A | 2/2000 | de la Rama et al. |
| 6,032,674 A | 3/2000 | Eggers et al. |
| 6,033,403 A | 3/2000 | Tu et al. |
| 6,042,580 A | 3/2000 | Simpson |
| 6,045,550 A | 4/2000 | Simpson et al. |
| 6,048,329 A | 4/2000 | Thompson et al. |
| 6,049,737 A | 4/2000 | Simpson et al. |
| 6,050,994 A | 4/2000 | Sherman |
| 6,052,612 A | 4/2000 | Desai |
| 6,053,937 A | 4/2000 | Edwards et al. |
| 6,056,744 A | 5/2000 | Edwards |
| 6,059,778 A | 5/2000 | Sherman |
| 6,063,077 A | 5/2000 | Schaer |
| 6,063,082 A | 5/2000 | DeVore et al. |
| 6,064,902 A | 5/2000 | Haissaguerre et al. |
| 6,068,629 A | 5/2000 | Haissaguerre et al. |
| 6,070,094 A | 5/2000 | Swanson et al. |
| 6,071,274 A | 6/2000 | Thompson et al. |
| 6,071,279 A | 6/2000 | Whayne et al. |
| 6,071,281 A | 6/2000 | Burnside et al. |
| 6,071,282 A * | 6/2000 | Fleischman .................. 606/41 |
| 6,074,351 A | 6/2000 | Houser |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson et al. |
| 6,106,522 A | 8/2000 | Fleischman et al. |
| 6,107,699 A | 8/2000 | Swanson |
| 6,115,626 A | 9/2000 | Whayne et al. |
| 6,119,041 A | 9/2000 | Pomeranz et al. |
| 6,120,476 A | 9/2000 | Fung et al. |
| 6,129,724 A | 10/2000 | Fleischman et al. |
| 6,141,576 A | 10/2000 | Littmann et al. |
| 6,146,379 A | 11/2000 | Fleischman et al. |
| 6,146,381 A | 11/2000 | Bowe et al. |
| 6,165,169 A | 12/2000 | Panescu et al. |
| 6,167,291 A | 12/2000 | Barajas et al. |
| 6,171,305 B1 | 1/2001 | Sherman |
| 6,171,306 B1 | 1/2001 | Swanson et al. |
| 6,179,833 B1 | 1/2001 | Taylor |
| 6,200,314 B1 | 3/2001 | Sherman |
| 6,212,426 B1 | 4/2001 | Swanson |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,573 B1 | 4/2001 | Webster |
| 6,217,576 B1 | 4/2001 | Tu et al. |
| 6,226,542 B1 | 5/2001 | Reisfeld |
| 6,231,570 B1 | 5/2001 | Tu et al. |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,725 B1 | 6/2001 | Cosman |
| 6,241,726 B1 | 6/2001 | Raymond et al. |
| 6,241,727 B1 | 6/2001 | Tu et al. |
| 6,241,728 B1 | 6/2001 | Gaiser et al. |
| 6,241,754 B1 | 6/2001 | Swanson et al. |
| 6,245,067 B1 | 6/2001 | Tu et al. |
| 6,245,089 B1 | 6/2001 | Daniel et al. |
| 6,251,107 B1 | 6/2001 | Schaer |
| 6,256,540 B1 | 7/2001 | Panescu et al. |
| 6,264,664 B1 | 7/2001 | Avellanet |
| 6,267,746 B1 | 7/2001 | Bumbalough |
| 6,290,697 B1 | 9/2001 | Tu et al. |
| 6,293,943 B1 | 9/2001 | Panescu et al. |
| 6,302,880 B1 | 10/2001 | Schaer |
| 6,309,385 B1 | 10/2001 | Simpson |
| 6,312,425 B1 | 11/2001 | Simpson et al. |
| 6,319,251 B1 | 11/2001 | Tu et al. |
| 6,325,797 B1 | 12/2001 | Stewart et al. |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson |
| 6,360,128 B2 | 3/2002 | Kordis et al. |
| 6,370,435 B2 | 4/2002 | Panescu et al. |
| 6,371,955 B1 | 4/2002 | Fuimaono et al. |
| 6,379,352 B1 | 4/2002 | Reynolds et al. |
| 6,389,311 B1 | 5/2002 | Whayne et al. |
| 6,391,024 B1 | 5/2002 | Sun et al. |
| 6,425,894 B1 | 7/2002 | Brucker et al. |
| 6,428,536 B2 | 8/2002 | Panescu et al. |
| 6,428,537 B1 | 8/2002 | Swanson et al. |
| 6,440,129 B1 | 8/2002 | Simpson |
| 6,447,506 B1 | 9/2002 | Swanson et al. |
| 6,451,015 B1 | 9/2002 | Rittman, III et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,693 B1 | 10/2002 | Carroll et al. |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest et al. |
| 6,478,793 B1 | 11/2002 | Cosman et al. |
| 6,485,487 B1 | 11/2002 | Sherman |
| 6,487,441 B1 | 11/2002 | Swanson et al. |
| 6,488,678 B2 | 12/2002 | Sherman |
| 6,490,468 B2 | 12/2002 | Panescu et al. |
| 6,493,586 B1 | 12/2002 | Stahmann et al. |
| 6,500,167 B1 | 12/2002 | Webster, Jr. |
| 6,500,172 B1 | 12/2002 | Panescu et al. |
| 6,514,246 B1 | 2/2003 | Swanson et al. |
| 6,517,536 B2 | 2/2003 | Hooven et al. |
| 6,522,905 B2 | 2/2003 | Desai |
| 6,529,756 B1 | 3/2003 | Phan et al. |
| 6,540,744 B2 | 4/2003 | Hassett et al. |
| 6,542,773 B2 | 4/2003 | Dupree et al. |
| 6,544,262 B2 | 4/2003 | Fleischman |
| 6,551,271 B2 | 4/2003 | Nguyen |
| 6,554,794 B1 | 4/2003 | Mueller et al. |
| 6,558,378 B2 | 5/2003 | Sherman et al. |
| 6,565,511 B2 | 5/2003 | Panescu et al. |
| 6,569,114 B2 | 5/2003 | Ponzi et al. |
| 6,569,162 B2 | 5/2003 | He |
| 6,569,163 B2 | 5/2003 | Hata et al. |
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,583,796 B2 | 6/2003 | Jamar et al. |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,607,520 B2 | 8/2003 | Keane |
| 6,616,657 B2 | 9/2003 | Simpson et al. |
| 6,625,482 B1 | 9/2003 | Panescu et al. |

(56) References Cited

U.S. PATENT DOCUMENTS

| | | |
|---|---|---|
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,223 B2 | 10/2003 | Lifshitz et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,652,517 B1 | 11/2003 | Hall et al. |
| 6,658,279 B2 | 12/2003 | Swanson et al. |
| 6,669,692 B1 | 12/2003 | Nelson et al. |
| 6,669,693 B2 | 12/2003 | Friedman |
| 6,671,533 B2 | 12/2003 | Chen et al. |
| 6,690,972 B2 | 2/2004 | Conley et al. |
| 6,701,180 B1 | 3/2004 | Desai |
| 6,702,811 B2 | 3/2004 | Stewart et al. |
| 6,711,428 B2 | 3/2004 | Fuimaono et al. |
| 6,730,078 B2 | 5/2004 | Simpson et al. |
| 6,738,673 B2 | 5/2004 | Desai |
| 6,740,080 B2 | 5/2004 | Jain et al. |
| 6,743,225 B2 | 6/2004 | Sanchez et al. |
| 6,746,446 B1 | 6/2004 | Hill, III et al. |
| 6,752,804 B2 | 6/2004 | Simpson et al. |
| 6,761,716 B2 | 7/2004 | Kadhiresan et al. |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,866,662 B2 | 3/2005 | Fuimaono et al. |
| 6,893,438 B2 | 5/2005 | Hall et al. |
| 6,893,439 B2 | 5/2005 | Fleischman |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 | 10/2005 | Satake |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 12/2005 | Hill, III et al. |
| 6,973,339 B2 | 12/2005 | Govari |
| 6,987,995 B2 | 1/2006 | Drysen |
| 7,001,336 B2 | 2/2006 | Mandrusov et al. |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Fuimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai et al. |
| 7,155,270 B2 | 12/2006 | Solis et al. |
| 7,156,843 B2 | 1/2007 | Skarda |
| 7,163,537 B2 | 1/2007 | Lee et al. |
| 7,429,261 B2 * | 9/2008 | Kunis et al. ............ 606/41 |
| 7,857,808 B2 * | 12/2010 | Oral et al. ............. 606/41 |
| 2001/0029366 A1 | 10/2001 | Swanson et al. |
| 2001/0039415 A1 | 11/2001 | Francischelli et al. |
| 2001/0044625 A1 | 11/2001 | Hata et al. |
| 2001/0051803 A1 | 12/2001 | Desai et al. |
| 2002/0065465 A1 | 5/2002 | Panescu et al. |
| 2002/0120263 A1 | 8/2002 | Brown et al. |
| 2002/0126036 A1 | 9/2002 | Flaherty et al. |
| 2002/0161422 A1 | 10/2002 | Swanson et al. |
| 2003/0018330 A1 | 1/2003 | Swanson et al. |
| 2003/0093069 A1 | 5/2003 | Panescu et al. |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman et al. |
| 2003/0199746 A1 | 10/2003 | Fuimaono et al. |
| 2003/0204185 A1 | 10/2003 | Sherman et al. |
| 2003/0204186 A1 | 10/2003 | Geistert |
| 2004/0015164 A1 | 1/2004 | Fuimaono et al. |
| 2004/0082947 A1 | 4/2004 | Oral et al. |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Bednarek |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfery |
| 2004/0236324 A1 | 11/2004 | Muller et al. |
| 2004/0247164 A1 | 12/2004 | Furnish |
| 2005/0010095 A1 | 1/2005 | Stewart et al. |
| 2005/0015084 A1 | 1/2005 | Hill et al. |
| 2005/0033137 A1 | 2/2005 | Oral et al. |
| 2005/0065512 A1 | 3/2005 | Schaer |
| 2005/0096644 A1 | 5/2005 | Hall et al. |
| 2005/0101946 A1 | 5/2005 | Govari et al. |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 * | 4/2006 | Werneth et al. ............ 606/41 |
| 2006/0095030 A1 | 5/2006 | Avitall et al. |
| 2006/0106375 A1 | 5/2006 | Werneth et al. |
| 2006/0111700 A1 | 5/2006 | Kunis et al. |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0142753 A1 | 6/2006 | Francischelli et al. |
| 2006/0189975 A1 | 8/2006 | Whayne et al. |
| 2006/0195082 A1 | 8/2006 | Francischelli |
| 2006/0241366 A1 | 10/2006 | Falwell et al. |
| 2007/0083193 A1 | 4/2007 | Werneth et al. |
| 2007/0083194 A1 | 4/2007 | Kunis et al. |
| 2007/0083195 A1 | 4/2007 | Werneth et al. |
| 2007/0106293 A1 | 5/2007 | Oral et al. |

FOREIGN PATENT DOCUMENTS

| | | |
|---|---|---|
| CA | 2327518AA | 11/1999 |
| CA | 2328064AA | 11/1999 |
| CA | 2328070AA | 11/1999 |
| CA | 2371935AA | 12/2000 |
| CA | 2222617 C | 7/2002 |
| CA | 2437140AA | 6/2004 |
| CA | 2492283AA | 7/2005 |
| CA | 2194061 C | 4/2006 |
| CA | 2276755 C | 5/2006 |
| CA | 2251041 C | 6/2006 |
| EP | 428812 B1 | 3/1995 |
| EP | 779059 A | 6/1997 |
| EP | 598742 B1 | 8/1999 |
| EP | 879016 B1 | 10/2003 |
| EP | 1360938 A1 | 11/2003 |
| EP | 1364677 A2 | 11/2003 |
| EP | 1554986 A1 | 7/2005 |
| EP | 823843 B1 | 10/2005 |
| EP | 1384445 B1 | 2/2006 |
| EP | 1169976 B1 | 4/2006 |
| EP | 1415680 B1 | 4/2006 |
| EP | 1011437 B1 | 5/2006 |
| EP | 1210021 B1 | 5/2006 |
| EP | 1658818 A1 | 5/2006 |

(56) References Cited

FOREIGN PATENT DOCUMENTS

| | | | |
|---|---|---|---|
| EP | 1125549 | B1 | 6/2006 |
| EP | 1182980 | B1 | 6/2006 |
| EP | 1207798 | B1 | 6/2006 |
| EP | 1321166 | B1 | 7/2006 |
| EP | 1343427 | B1 | 7/2006 |
| EP | 828451 | B1 | 9/2006 |
| EP | 1070480 | B1 | 9/2006 |
| EP | 1014874 | B1 | 12/2006 |
| EP | 1383437 | B1 | 12/2006 |
| EP | 1455667 | B1 | 1/2007 |
| EP | 957794 | B1 | 7/2007 |
| JP | 2004188179 | A | 7/2004 |
| SU | 1512622 | A1 | 10/1989 |
| SU | 1544396 | A1 | 2/1990 |
| SU | 1690786 | A1 | 11/1991 |
| WO | WO90/06079 | A1 | 6/1990 |
| WO | WO93/08756 | A1 | 5/1993 |
| WO | WO93/25273 | A1 | 12/1993 |
| WO | WO94/12098 | A1 | 6/1994 |
| WO | WO96/10961 | A1 | 4/1996 |
| WO | WO96/32885 | A1 | 10/1996 |
| WO | WO96/32897 | A1 | 10/1996 |
| WO | WO96/34558 | A1 | 11/1996 |
| WO | WO96/34559 | A1 | 11/1996 |
| WO | WO96/34560 | A1 | 11/1996 |
| WO | WO96/34567 | A1 | 11/1996 |
| WO | WO96/34569 | A1 | 11/1996 |
| WO | WO96/34570 | A1 | 11/1996 |
| WO | WO96/34650 | A1 | 11/1996 |
| WO | WO96/34652 | A1 | 11/1996 |
| WO | WO96/34653 | A1 | 11/1996 |
| WO | WO96/36860 | A2 | 11/1996 |
| WO | WO96/39967 | A1 | 12/1996 |
| WO | WO97/15919 | A1 | 5/1997 |
| WO | WO97/17893 | A1 | 5/1997 |
| WO | WO97/17904 | A1 | 5/1997 |
| WO | WO97/25917 | A1 | 7/1997 |
| WO | WO97/25919 | A1 | 7/1997 |
| WO | WO97/32525 | A1 | 9/1997 |
| WO | WO97/36541 | A1 | 10/1997 |
| WO | WO97/40760 | A1 | 11/1997 |
| WO | WO97/42996 | A1 | 11/1997 |
| WO | WO98/18520 | A2 | 5/1998 |
| WO | WO98/19611 | A1 | 5/1998 |
| WO | WO98/26724 | A1 | 6/1998 |
| WO | WO98/28039 | A2 | 7/1998 |
| WO | WO98/38913 | A1 | 9/1998 |
| WO | WO99/02096 | A1 | 1/1999 |
| WO | WO99/56644 | A1 | 11/1999 |
| WO | WO99/56647 | A1 | 11/1999 |
| WO | WO99/56648 | A1 | 11/1999 |
| WO | WO99/56649 | A1 | 11/1999 |
| WO | WO00/78239 | A2 | 12/2000 |
| WO | WO02/060523 | A2 | 8/2002 |
| WO | WO03/041602 | A2 | 5/2003 |
| WO | WO03/089997 | A2 | 10/2003 |
| WO | WO2005/027765 | A1 | 3/2005 |
| WO | WO2005/027766 | A1 | 3/2005 |
| WO | WO2005/065562 | A1 | 7/2005 |
| WO | WO2005/065563 | A1 | 7/2005 |
| WO | WO2005/104972 | A2 | 11/2005 |
| WO | WO2006/017517 | A2 | 2/2006 |
| WO | WO2006/044794 | A2 | 4/2006 |
| WO | WO2006/049970 | A2 | 5/2006 |
| WO | WO2006/052651 | A1 | 5/2006 |
| WO | WO2006/052905 | A2 | 5/2006 |
| WO | WO2006/055654 | A1 | 5/2006 |
| WO | WO2006/055658 | A1 | 5/2006 |
| WO | WO2006/055733 | A1 | 5/2006 |
| WO | WO2006/055741 | A1 | 5/2006 |

OTHER PUBLICATIONS

"Werneth et al.; U.S. Appl. No. 12/116,753 entitled""Ablation therapy system and method for treating continuous atrial fibrillation,""filed May 7, 2008".

Sherman et. al. ; U.S. Appl. No. 12/117,596 entitled "RF energy delivery system and method," filed May 8, 2008.

Kunis et al.; U.S. Appl. No. 12/197,425 entitled "Atrial ablation catheter and method of use," filed Aug. 25, 2008.

Werneth et al.; U.S. Appl. No. 12/245,625 entitled "Ablation catheter," filed Oct. 3, 2008.

Nademanee et al., "A new approach for catheter ablation of atrial fibrillation: mapping of the electrophysiologic substrate," JACC, vol. 43, No. 11, pp. 2044-2053, 2004.

Wittkampf et al., "Radiofrequency ablation with a cooled porous electrode catheter," (abstract) JACC, vol. 11, No. 2, pp. 17a, Feb. 1988.

\* cited by examiner

Fig. 1
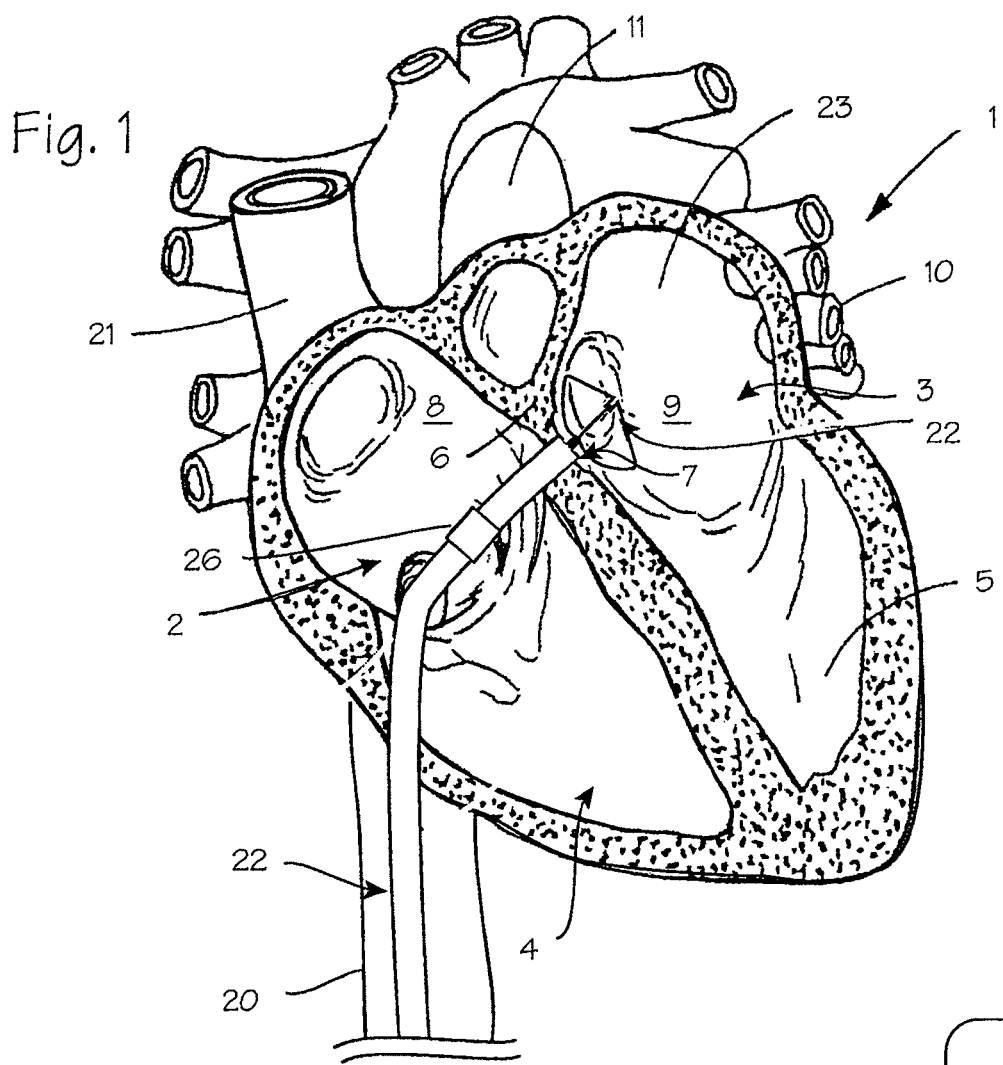
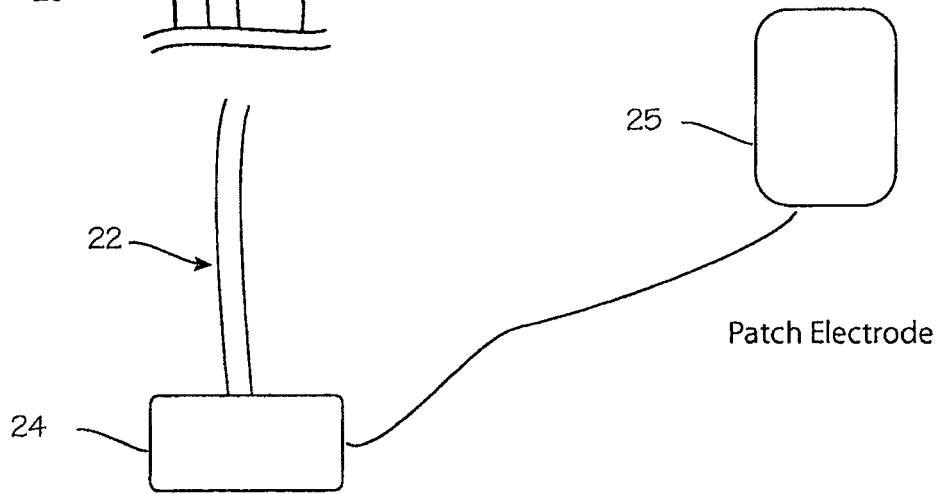
Control System
Patch Electrode

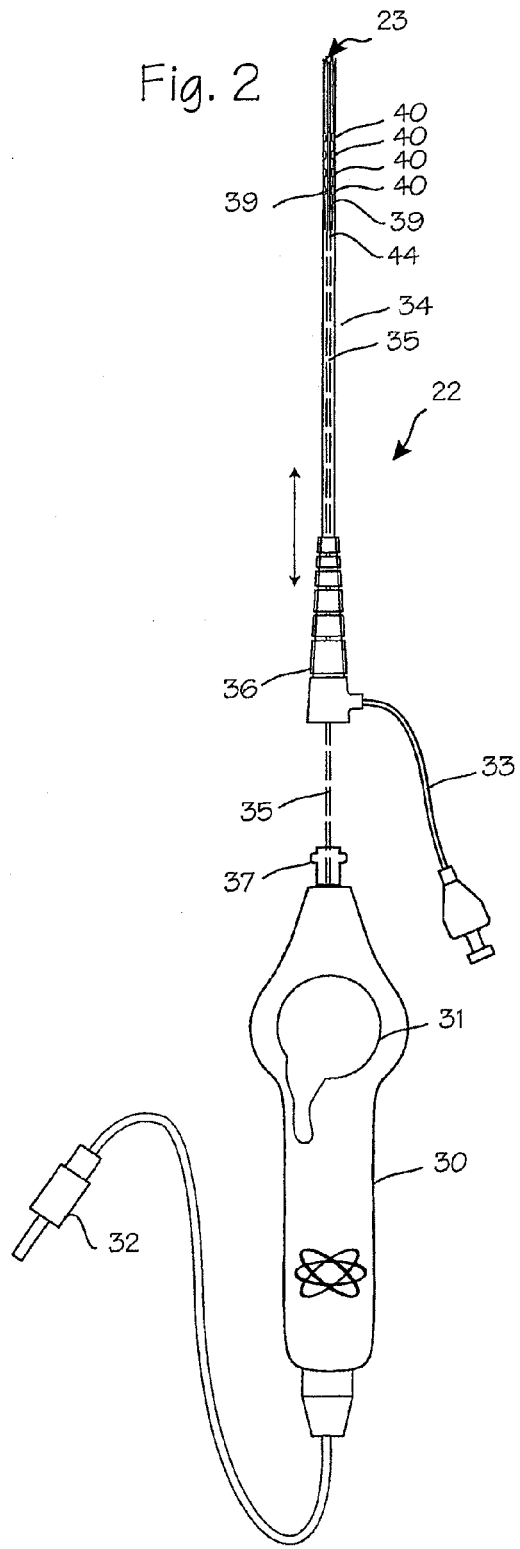
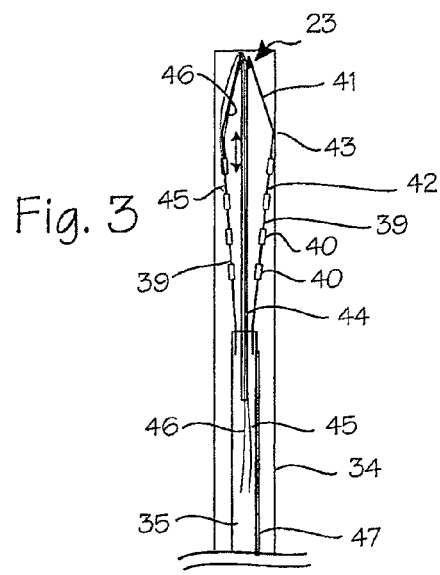
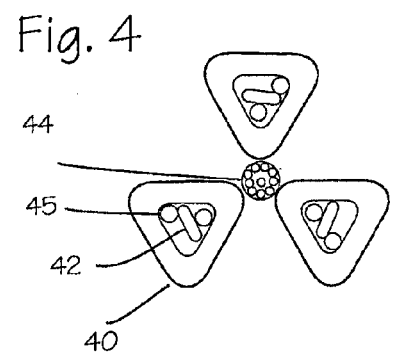

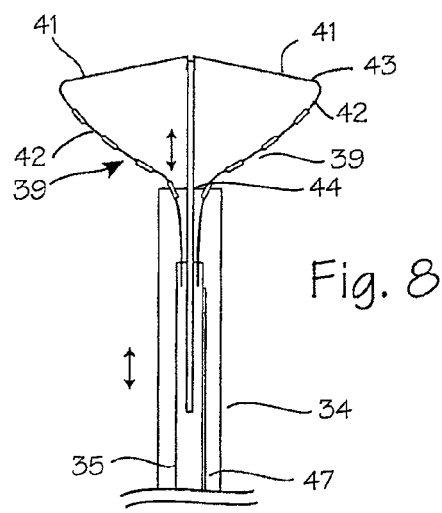
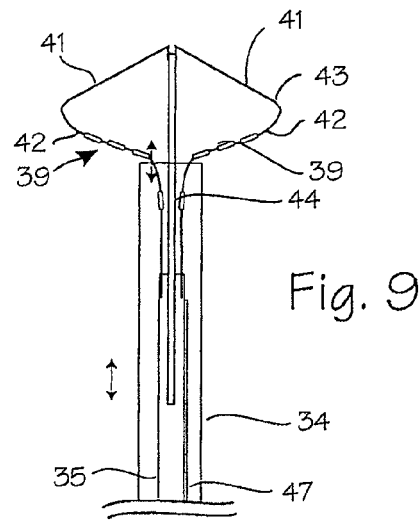
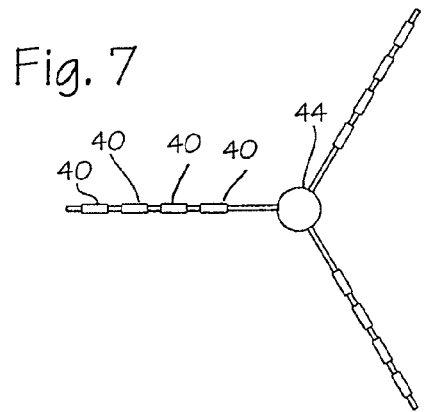
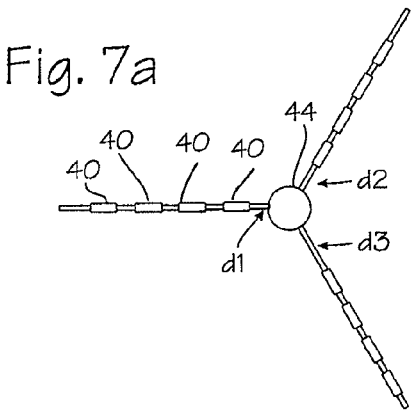

SAGITTATE right wall of left atrium

ATRIAL ABLATION CATHETER ADAPTED FOR TREATMENT OF SEPTAL WALL ARRHYTHMOGENIC FOCI AND METHOD OF USE

CROSS REFERENCE TO RELATED APPLICATIONS

This application is a continuation of U.S. patent application Ser. No. 10/997,713, filed Nov. 24, 2004, and entitled "Atrial Ablation Catheter Adapted for Treatment of Septal Wall Arrhythmogenic Foci and Method of Use", now U.S. Pat. No. 7,468,062, issued Dec. 23, 2008.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The inventions described below relate the field of atrial ablation.

BACKGROUND OF THE INVENTION

Atrial fibrillation is a form of arrhythmia, or irregular heartbeat, in which the atria (the two small upper chambers of the heart) quiver instead of beating effectively. While there are a number of variations of atrial fibrillation with different causes, they all involve irregularities in the transmission of electrical impulses through the heart. As a result of abnormalities in the heart's electrical impulses, the heart is not able to pump the blood out properly, and it may pool and clot. If a blood clot moves to an artery in the brain, AF can lead to stroke. AF is also associated with increased risks of congestive heart failure and cardiomyopathy. These risks warrant medical attention for patients with AF even if the symptoms are mild. Atrial fibrillation is the most common sustained heart rhythm disorder and increases the risk for heart disease and stroke, both leading causes of death in the United States. Over 2 million adults in the United States have been diagnosed with atrial fibrillation.

Various ablation techniques have been proposed to treat atrial fibrillation, including the Cox-Maze procedure, linear ablation of various regions of the atrium, and circumferential pulmonary vein ablation. Each of these techniques has its various drawbacks. The Cox-Maze procedure and linear ablation procedures are tedious and time-consuming, taking up to several hours to accomplish endocardially. Circumferential ablation is proving to lead to rapid stenosis and occlusion of the pulmonary veins, and of course is not applicable to treatment of the septal wall of the left atrium. The catheter mounted electrode arrays described in our co-pending patent application Kunis, et al., Atrial Ablation Catheter and Method of Use, U.S. application Ser. No. 10/997,172 filed Nov. 22, 2004 provide for more efficient and effective treatment of atrial fibrillation. The treatment of the septal wall is facilitated with the devices and methods described below, which permit septal wall treatment from a percutaneous venous access route without the need to maneuver a distally facing electrode array in apposition to the septal wall.

SUMMARY OF THE INVENTION

The devices and methods described below provide for a simplified approach to the treatment of atrial fibrillation with substantially improved efficacy and outcomes in patients with paroxysmal or persistent atrial fibrillation, especially for those arrhythmia originating from, or sustained by, arrhythmogenic foci located on the septal wall of the left atrium. An endocardial catheter with an electrode array particularly adapted to locate and ablate foci of arrhythmia which are required for sustained atrial fibrillation is provided. The array is easily deployed and retracted from the catheter, and presents a proximally oriented electrode array that can be pulled against the septal wall of the left atrium to engage the septal wall. A control system comprising an ECG analyzer and a RF power supply operates to analyze electrical signals obtained from the electrode array, determine if an arrhythmogenic focus is present in the area covered by the array, and supply RF power to appropriate electrodes to ablate the focus.

BRIEF DESCRIPTION OF THE DRAWINGS

FIG. 1 illustrates the treatment to be accomplished with the devices and methods described below.

FIG. 2 illustrates an atrial sensing and ablation catheter with an expandable electrode array constrained within an outer catheter tube.

FIG. 3 is an enlarged view of the distal portion of the catheter of FIG. 2.

FIG. 4 is a cross-section of the distal portion of the catheter of FIG. 2.

FIG. 7 is an end view of the electrode array in its expanded configuration.

FIG. 7a is an end view of the electrode array, with an asymmetric arrangement of electrodes, in its expanded configuration.

FIGS. 8 and 9 illustrate the mechanism of recapture of the electrode array of the atrial ablation catheter.

FIG. 10b illustrates the meaning of the terminology which precisely defines the electrode array of FIGS. 10 and 10a.

DETAILED DESCRIPTION OF THE INVENTION

Figure 5:
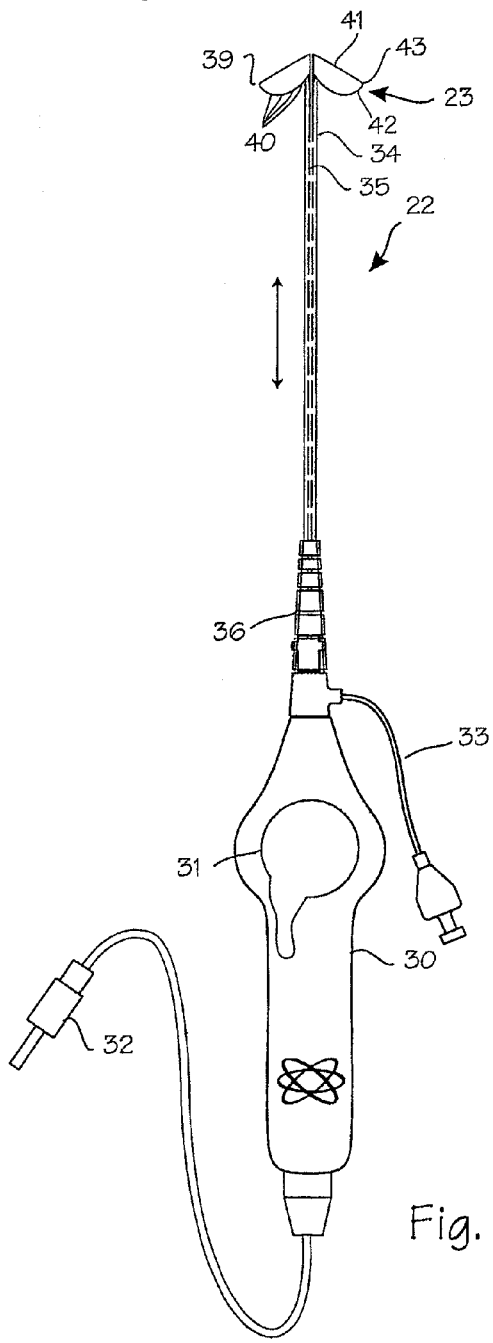
FIG. 5 illustrates the atrial sensing and ablation catheter of FIG. 2 with the electrode array in its expanded configuration.

FIG. 1 illustrates the treatment to be accomplished with the devices and methods described below. FIG. 1 shows a cut-away view of the human heart 1, showing the major structures of the heart including the right atrium 2, the left atrium 3, the right ventricle 4, and the left ventricle 5. The atrial septum 6 separates the left and right atria. The fossa ovalis 7 is a small depression in the atrial septum which is easily punctured and easily heals. The percutaneous venous approach through the right atrium and the fossa ovalis is the preferred access pathway to the left atrium. In a patient suffering from atrial fibrillation, aberrant electrically conductive tissue may be found in the atrial walls 8 and 9, including the septal wall surrounding the fossa ovalis, as well as in the pulmonary veins 10 and pulmonary arteries 11. These areas of aberrant electrically conductive tissue, referred to as arrhythmogenic foci, drivers or rotors, cause or sustain atrial fibrillation. Ablation of these areas is an effective treatment for atrial fibrillation. Though circumferential ablation of the pulmonary veins cures the arrhythmia which originates in the pulmonary veins, it often results in rapid stenosis of the pulmonary veins. Ablation of foci, rotors or drivers on atrial walls, however, may prevent the propagation of any aberrant electrical activity that originates in the pulmonary veins, originates in other regions of the atrial wall, or originates on the septal wall itself.

To accomplish ablation of the septal wall of the left atrium, a catheter is inserted into the atrium, preferably through the inferior vena cava 20, as shown in the illustration, or through the superior vena cava 21, into the right atrium and then into left atrium. When passing into the left atrium, as illustrated, the catheter penetrates the fossa ovalis (a trans-septal puncture will facilitate the crossing). The catheter 22 carries a distal electrode array 23 into the atrium, and this electrode array is adapted to be pulled into contact with the section of the atrial wall surrounding the fossa ovalis. The electrode array is electrically connected to circuitry in a control system 24 which is operable to analyze electrical signals detected by the electrodes and pass RF current through the electrodes and heart tissue to ablate the tissue. A surface electrode 25 is mounted on the patient's body (typically on the back) to permit use of the electrodes in monopolar modes. A return electrode 26 may also be provided on the catheter 22, proximal to the electrode array. Using the catheter, an electrophysiologist will map regions of the septal wall of the left atrium and apply energy through the catheter to ablate any arrhythmogenic foci which are identified in the mapping procedure. The procedure may be repeated as necessary on the septal wall, rotating the array if necessary, to ablate all detected foci.

FIG. 2 illustrates an atrial sensing and ablation catheter 22 with an expandable electrode array. The catheter comprises a handle 30 with a steering control knob 31, electrical connector 32 and side-arm connector 33. The electrical connector is used to connect the catheter to the control box. An outer catheter tube 34 is slidably mounted on the inner catheter tube 35, and they may be releasably secured to each other by sliding the proximal portion of the outer catheter sheath strain relief 36 over the cylindrical detent 37 which is fixed to the handle. The side arm connector is used as a flushing port, to allow the flushing of debris and blood from the space between the inner and outer catheter tubes. The electrode array 23 is fixed to the inner catheter tube 35, and is restrained within the distal portion of the outer catheter tube 34.

FIG. 3 is an enlarged view of the distal portion of the catheter of FIG. 2. The electrode array 23 comprises a number of resiliently biased arms 39 which each carry a number of electrodes 40. An array of three arms, each of which carry four electrodes, is suitable for use in the atria. The arms each comprise a wire (preferably a flat wire) with a distal section 41, a proximal section 42 and an intervening bend section 43. The electrodes are placed on the proximal sections. The proximal end of each arm is fixed to the inner catheter tube 35. The distal end of each arm is fixed to the floating tube (or pin) 44. This floating tube is retained within the inner catheter tube, but is free to slide longitudinally within the inner catheter tube. The necessary electrical wires 45 and 46 which connect the electrodes to the control system run from each electrode proximally along the arm (and through any intervening electrodes), and enter the lumen of the floating tube 44 and then run proximally through the inner catheter tube and into the catheter handle. (Additional wires for temperature sensing thermistor or thermocouples may be included.) The wires are looped within the handle to provide the distension necessary for the resilient deployment of the electrode array as illustrated in FIG. 5. A steering pull wire 47 is secured to the distal end of the inner catheter tube. The pull wire runs proximally to the steering control knob in the proximal handle, and is operably connected to the control knob so that rotation of the control knob pulls the pull wire to effectuate steering of the distal end of the device. The outer catheter tube is sufficiently flexible so that it is steered by deflection of the inner catheter tube. The materials used for each component are selected to provide the suitable flexibility, column strength and steerability. The outer catheter tube 34 may comprises nylon, polyester or other suitable polymer, and the inner catheter tube 35 comprises a stainless steel coil covered in shrink tubing to provide tensile strength. The electrode arms 39 comprise flat nitinol wires. The floating tube 44 comprises a stainless steel coil. The floating tube may be disposed over the inner catheter if accommodations are made for proximal fixation of the proximal arm segments to the inner catheter, such as placing the fixation points proximally on the inner catheter or providing slots on the proximal portion of the floating tube. The electrode wires may be disposed on or in the wall of the inner catheter, rather than passing through the lumen of the inner catheter as shown in the Figures.

Figure 6:
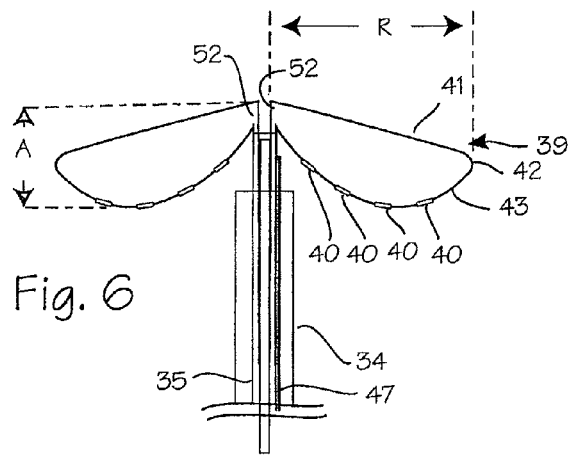
FIGS. 6 and 6a is an enlarged view of the electrode array in its expanded configuration.
Figure 6A:
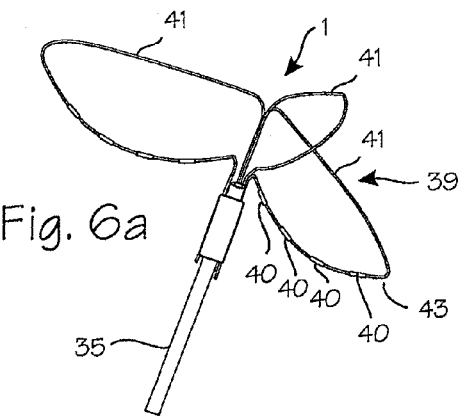

FIG. 4 is a cross-section of the proximal portion of the catheter of FIG. 2. At this cross section, an electrode 40 is mounted on each arm 39. These electrodes will be located on the proximally facing portion of the deployed array as shown in FIGS. 5 and 6. The electrodes are tubes of triangular cross section, with tissue contacting faces directed radially outwardly from the catheter. The electrode wires 45, which are connected to the inside electrodes, run through the outer electrodes on their route to the floating tube. The electrode wires 46 are fixed to the inner wall of the outer electrode. As shown in this view, the electrodes are collapsed upon the floating tube 44, and due to the triangular shape they are securely packed within the outer catheter tube 34. The floating tube 44 also houses the various electrode wires 45 and 46.

Figure 6B:
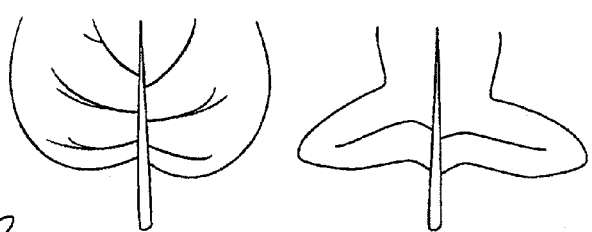
FIG. 6b illustrates the meaning of the terminology which precisely defines the electrode array of FIGS. 5 and 6

FIGS. 5 and 6 illustrate the atrial sensing and ablation catheter of FIG. 2 with the electrode array in its expanded configuration. The outer catheter tube 34 has been withdrawn proximally over the catheter inner tube, allowing the array arms 39 to expand to create array elements defining a substantially cordate or hastate proximal outline. The term cordate is used as it is in botany to describe a leaf with a base (where the leaf attaches to the stem) which is heart-shaped, having rounded lobes at the base which arch proximally away from the tip and then curve distally toward the tip of the leaf, as shown in FIG. 6b. The term hastate is also adopted from botany, and refers to proximally tending lobes with slightly curved proximal outlines and sharply bending tips, also as shown in FIG. 6b. In the array shown in FIGS. 5 and 6, the base of the array (the proximal portion analogous to the base of a leaf) is heart-shaped, having rounded lobes at the base which arch proximally away from the base and then curve outward and distally toward the tip of the array. Each proximal arm segment resiliently bends radially outwardly from the proximal connection with the inner catheter tube, bending sharply in the proximal direction before arching outwardly and distally, while each distal arm segment bends radially inwardly from the bend portion toward the longitudinally axis of the catheter.

The electrode array includes a number electrodes 40 mounted on the proximal section 42 of each array arm, and the distal section 41 need not have any electrodes disposed on it, as is shown. The overall shape of each arm is elongate on an axis perpendicular to the long axis of the catheter, having a radial length R which is several times the axial length A.

The resilient expansion of the electrode array pushes the floating tube 44 proximally into the inner catheter tube. When the outer catheter tube is pushed distally over the electrode array, the distal electrode arms will be forced distally, as the proximal segments are compressed inwardly starting from the proximal end, to first splay the distal segments toward and through a perpendicular relationship with the floating tube such that the joint between the arms and the floating tube is distal to the bend point, while drawing the floating tube distally within the inner catheter tube.

FIG. 7 is a proximal end view of the electrode array in its expanded configuration. In this view, the three-arm array is fully expanded resiliently. The array provides four electrodes on each of three arms evenly distributed about the floating tube 44. The electrode wires 45 and 46 (shown in FIG. 3) extend inwardly from the electrodes and run proximally down the floating tube. The arms are each separated from the adjacent arms by about 120°. The array, when deployed and flattened as shown, is preferably about 15 to 30 mm in diameter (to the outer extent of the arm), with each distal arm segment 41 being about 7.5 to 15 mm long. The diameter of the electrode group (from the center to the outer extent of the electrodes) is preferably about 2 to 30 mm. The wire width is preferable about 0.26 mm, and the distal face of the electrodes is preferably about 1 to 2 mm wide and 2 to 3 mm long (the illustrated electrodes are 2 mm wide and 1.6 mm wide). The electrode array can comprise any number of arms, and each arm can carry any number of electrodes, though the three arm array, with dimensions described above, is well suited for the septal wall ablation therapy. FIG. 7a is an end view of the electrode array, with an asymmetric arrangement of electrodes, in its expanded configuration. In this embodiment, each electrode is 2 mm long, and is fixed to the array arm with a 2 mm gap between adjacent electrodes. The inner electrode of the first set of electrodes 40a is placed at a distance of 2 mm (indicated by item d1) from the inner catheter tube 35 and each of the additional electrodes are placed with 2 mm gaps between each electrode, while the inner electrode of the second set of electrodes 40b is placed at a distance of 4 mm (indicated by item d2) from the inner catheter tube 35 and each of the additional electrodes are placed with 2 mm gaps between each electrode, and the inner electrode of the third set of electrodes 40c is placed at a distance of 6 mm (indicated by item d3) from the inner catheter tube 35 and each of the additional electrodes are placed with 2 mm gaps between each electrode. With the electrodes arranged in this asymmetric pattern on each of the otherwise symmetrical array arms, rotation of the array after ablation in one position will be less likely to result in seating the electrodes directly on a previously ablated section of the septal wall.

FIGS. 8 and 9 illustrate the mechanism of recapture of the electrode array. When the outer catheter tube 34 is pushed distally over the inner catheter tube 35 and the electrode array, the distal electrode arms 41 will be forced distally, as the proximal segments 42 are compressed inwardly starting from the proximal end, as shown in FIG. 8. This initially splays the distal segments toward a perpendicular relationship with the floating tube as shown in FIG. 8. As the outer catheter tube is translated further distally, such that the joint between the arms and the floating tube is distal to the bend point, the distal arm segments become further splayed, such that they are distal to the proximal arms segments. Because the distal arm segments are fixed to the floating tube, their movement distally draws the floating tube distally within the inner catheter tube. The array is completely captured when the outer catheter tube is translated fully forward to resume the position shown in FIGS. 2 and 3. As can be seen from the illustration, the bend sections provide a means for rotatably joining the distal arm segment to the proximal arm segment, and other suitable mechanisms, such as hinges, may be used instead.

Figure 10:
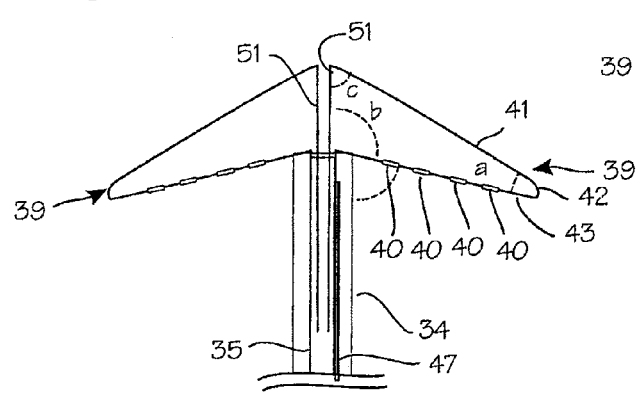
FIGS. 10 and 10a illustrates an alternate geometry of the septal wall array.
Figure 10A:
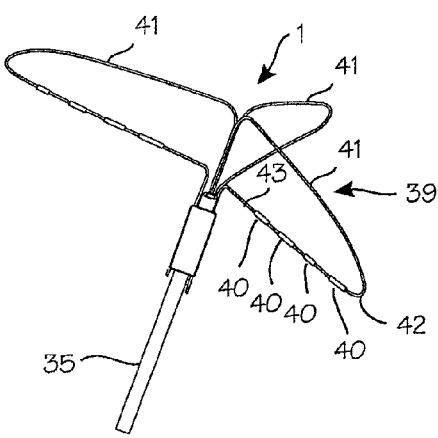
Figure 10B:
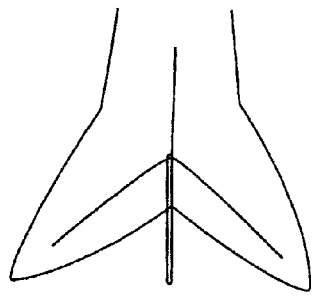

FIGS. 10 and 10a illustrate an alternate geometry of the septal wall array. The outer catheter tube 34 has been withdrawn proximally over the catheter inner tube, allowing the array arms 39 to expand to create array elements defining a substantially sagittate proximal outline. We use the term sagittate as that term is used in botany, where it describes a leaf with a base (where the leaf attaches to the stem) which is arrow-shaped (the back end of the arrow), having sharply triangular lobes with generally straight sides at the base which bend proximally away from the tip and then sharply turn distally toward the tip of the leaf, as shown in FIG. 10b. Here, the array arms have sharply triangular lobes at the base which bend proximally away from the catheter and then sharply turn distally toward the tip of the array. Each proximal arm segment resiliently bends radially outwardly from the proximal connection with the inner catheter tube, bending sharply in the proximal direction, while each distal arm segment bends radially inwardly from the bend portion toward the longitudinally axis of the catheter. The floating tube 44 of FIG. 6 need not be used, as in this example the array distal arm segments are joined at their extreme distal ends to floating pins 51 which comprise proximally running segments that enter the inner catheter tube to provide the floating attachment of the distal arm segments to the catheter body. (Thus both floating pin or arm extensions, or the floating tube, and other suitable means, may be used to fix the distal end of the electrode arms in a radially central area while leaving the distal ends of the electrode arms freely translatable along the catheter longitudinal axis.) The electrode array can be restrained within the outer catheter tube, released and recaptured by sliding the outer catheter proximally or distally.

Figure 11:
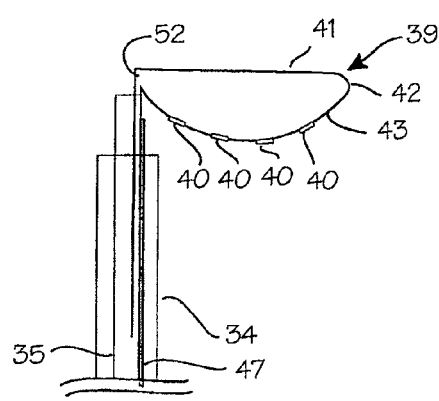
FIGS. 11, 12 and 13 illustrate additional alternative geometries of the array.
Figure 12:
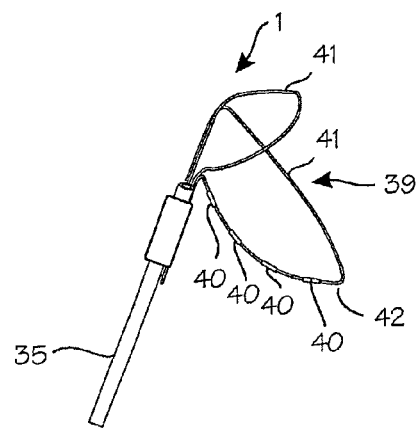
Figure 13:
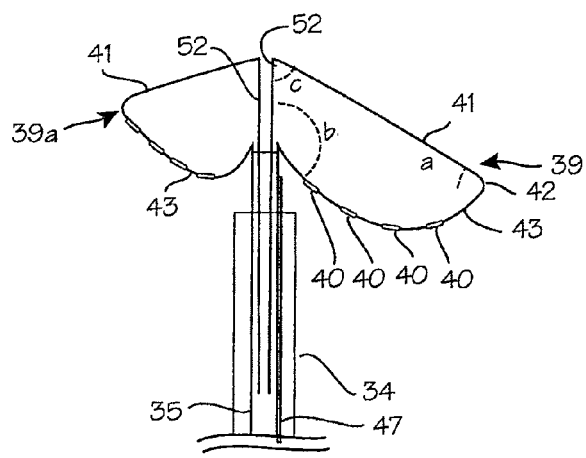

FIGS. 11, 12 and 13 illustrate additional alternative geometries of the array. In each device, the overall shape of the array arms may be as shown in any of the previous figures, but the array is asymmetrical or oblique. In FIG. 11, the array consists of a single arm 39, while in FIG. 12 the array comprises two arms disposed at a slight angle to each other, so that the array is radially asymmetrical. In FIG. 13, the array comprises an array arms 39 and 39a which are of substantial different sized, resulting in an oblique arrangement. Again, the term oblique is borrowed from botany, where it refers to leaves with lopsided proximal lobes, very similar to the lopsided proximal outlines of the array arms in FIG. 13. These arrays may be used where the anatomy of a particular patient's atrium demands, as where the fossa ovalis is positioned very near an upper or lower wall which would prevent full deployment of a symmetrical array.

Figure 14:
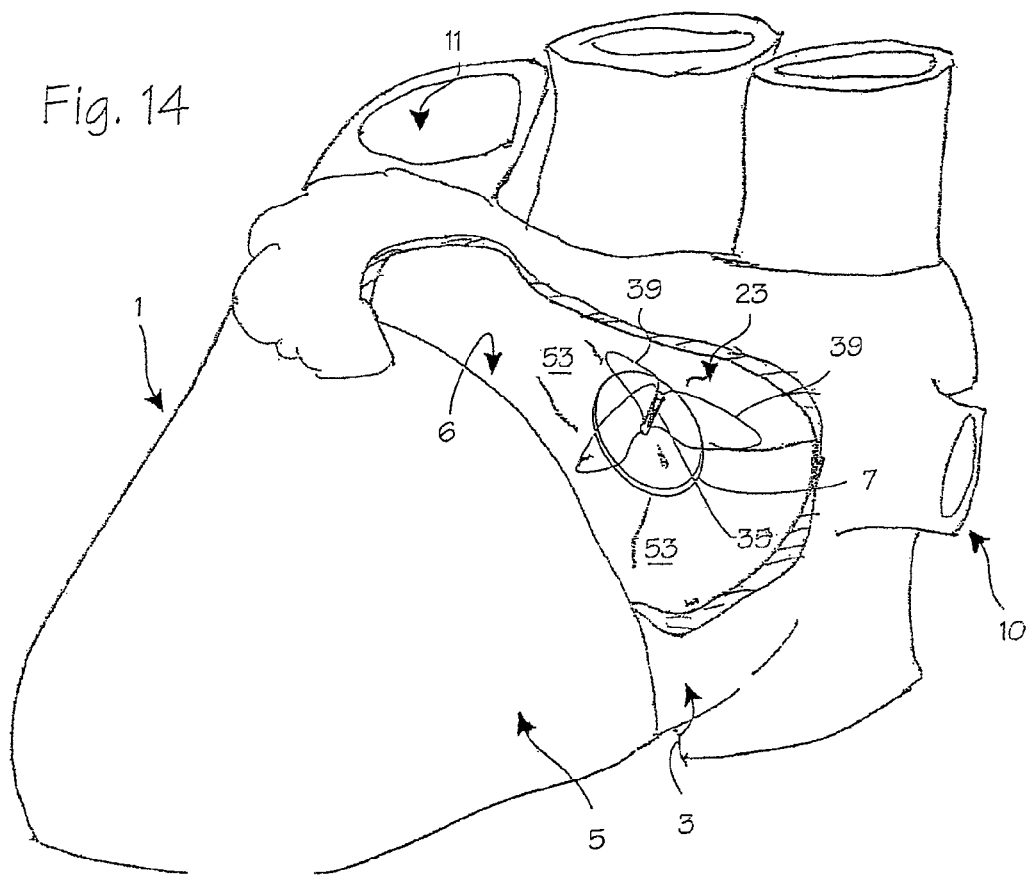
FIGS. 14 and 15 illustrate the method of using the device of to treat the septal wall of the left atrium.
Figure 15:
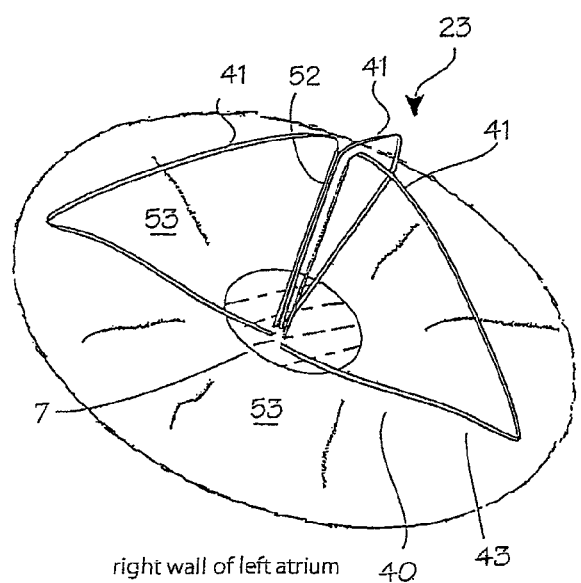

FIGS. 14 and 15 illustrate the method of using the device of FIG. 6 or 10. FIG. 14 shows the heart 1 from the left side, showing the left atrium 3, the left ventricle 5, pulmonary veins 10, pulmonary artery 11. The left atrium is shown in a cutaway view, in which the atrial septum 6 and its left atrial surface 53 and the fossa ovalis 7 are shown. To treat arrhythmogenic foci, drivers or rotors on the septal wall near the fossa ovalis, the distal end of the catheter of FIG. 6 or 10 is inserted through the fossa ovalis (via the transeptal approach from the right atrium). Thereafter, the outer catheter is withdrawn, so that the electrode array arms 39 resiliently expand to the configuration in which the proximal arm segments are substantially parallel or slightly reflexed relative to the long axis of the catheter. As shown in FIG. 15, to engage the septal wall, the electrode array is pulled proximally into contact with the septal wall, by pulling proximally on the catheter inner tube 35. As shown, the array will deform, forcing the distal arm segments 41 to splay distally, drawing the floating posts or pins 51 distally in response to the deformation of the array, while at the same time resiliently biasing the proximal arm segments 42 and the electrodes 40 against the septal wall 53 of the left atrium.

After contact has been established between the atrium wall and the electrode array, the operator will analyze electrical signals detected by the electrodes to determine if the array has been placed over an arrhythmogenic focus. If it has, the operator may energize any of the electrodes, as appropriate, to ablate the focus. Bipolar RF energy may be applied between pairs of the electrodes, or monopolar energy may be applied to any of the electrodes (grounded to the surface electrode or a return electrode located proximally on the catheter body). The array may moved off the septal wall, rotated slightly, and reseated against the septal wall to test and treat the entire area surrounding the fossa ovalis with just a few array arms (alternatively, the array may be provided with many arms, such that the electrode density it sufficient to find an ablate all significant foci within its footprint). Linear lesions may be created using the electrodes along a single proximal arm, operating the electrodes in bipolar mode, and other therapeutic lesions may be created using electrodes pairs established between the electrodes of one arm and the electrodes of another arm, operating such pairs in bipolar mode, or operating electrodes in conjunction with return electrodes in a monopolar mode.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. An ablation catheter configured to ablate septal wall tissue, comprising:
    an elongate delivery tube defining a major axis and having a distal end adapted for insertion into the heart of a patient;
    at least one resilient arm with a delivery configuration and an expanded configuration, wherein the at least one resilient arm comprises a distal arm section, a proximal arm section, and a bend section disposed between the distal arm section and the proximal arm section, the proximal arm section of the at least one resilient arm defining a shape selected from the group consisting of cordate, hastate, and sagittate when the at least one resilient arm is in the expanded configuration; and
    a plurality of electrodes disposed on the proximal arm section of the at least one resilient arm, wherein the distal arm section defines a substantially linear configuration substantially orthogonal to the major axis when the at least one resilient arm is in the expanded configuration.

2. The ablation catheter of claim 1 wherein the at least one resilient arm is adapted to bend at the bend section when it is expanded from the delivery configuration to the expanded configuration.

3. The ablation catheter of claim 1 wherein the proximal arm section forms an acute angle with the distal arm section at the bend section when the at least one resilient arm is in the expanded configuration.

4. The ablation catheter of claim 1 further comprising a pin extending into the elongate delivery tube, the pin being longitudinally slidable relative to the elongate delivery tube.

5. The ablation catheter of claim 4 wherein the proximal arm section is attached to the elongate delivery tube and the distal arm section is attached to the pin.

6. The ablation catheter of claim 1 further adapted to map septal wall tissue.

7. The ablation catheter of claim 1 wherein the proximal arm section extends generally along a longitudinal axis of the elongate delivery tube when the at least one resilient arm is in the delivery configuration.

8. The ablation catheter of claim 1 wherein the distal arm section extends generally along a longitudinal axis of the elongate delivery tube when the at least one resilient arm is in the delivery configuration.

9. The ablation catheter of claim 1 wherein the proximal arm section is arcuate when the at least one resilient arm is in the expanded configuration.

10. An ablation catheter configured to ablate septal wall tissue, comprising:
    an elongate delivery tube having a distal end adapted for insertion into the heart of a patient;
    at least one resilient arm with a delivery configuration and an expanded configuration, wherein the at least one resilient arm comprises a distal arm section, a proximal arm section, and a bend section disposed between the distal arm section and the proximal arm section, the proximal arm section of the at least one resilient arm defining a shape selected from the group consisting of cordate, hastate, and sagittate when the at least one resilient arm is in the expanded configuration; and
    a plurality of electrodes disposed on the proximal arm section of the at least one resilient arm, wherein the bend section is pre-formed in the at least one resilient arm and forms an acute angle with the distal arm section.

11. The ablation catheter of claim 10 wherein the at least one resilient arm is adapted to bend at the bend section when it is expanded from the delivery configuration to the expanded configuration.

12. The ablation catheter of claim 10 further comprising a pin extending into the elongate delivery tube, the pin being longitudinally slidable relative to the elongate delivery tube.

13. The ablation catheter of claim 12 wherein the proximal arm section is attached to the elongate delivery tube and the distal arm section is attached to the pin.

14. The ablation catheter of claim 10 further adapted to map septal wall tissue.

15. The ablation catheter of claim 10 wherein the proximal arm section extends generally along a lateral axis of the elongate delivery tube when the at least one resilient arm is in the expanded configuration.

16. The ablation catheter of claim 10 wherein the distal arm section extends generally along a lateral axis of the elongate delivery tube when the at least one resilient arm is in the expanded configuration.

17. The ablation catheter of claim 10 wherein the proximal arm section extends generally along a longitudinal axis of the elongate delivery tube when the at least one resilient arm is in the delivery configuration.

18. The ablation catheter of claim 10 wherein the distal arm section extends generally along a longitudinal axis of the elongate delivery tube when the at least one resilient arm is in the delivery configuration.

19. The ablation catheter of claim 10 wherein the proximal arm section is arcuate when the at least one resilient arm is in the expanded configuration.

20. An ablation catheter configured to ablate septal wall tissue, comprising:
    an outer catheter tube defining a major axis and having a distal end adapted for insertion into the heart of a patient;
    an inner catheter tube slidably disposed within the outer catheter tube;

a pin slidably disposed within the inner catheter tube;
at least one resilient arm with a delivery configuration and an expanded configuration, wherein the at least one resilient arm comprises a distal arm section attached to the pin, a proximal arm section attached to the inner catheter tube, and a bend section disposed between the distal arm section and the proximal arm section,
wherein the distal arm section defines a substantially linear configuration substantially orthogonal to the major axis when the at least one resilient arm is in the expanded configuration, and proximal arm section of the at least one resilient arm defines a shape selected from the group consisting of cordate, hastate, and sagittate when the at least one resilient arm is in the expanded configuration; and
a plurality of electrodes disposed on the proximal arm section of the at least one resilient arm.

21. The ablation catheter of claim 20 wherein the at least one resilient arm is adapted to bend at the bend section when it is expanded from the delivery configuration to the expanded configuration.

22. The ablation catheter of claim 20 further adapted to map the septal wall.

23. The ablation catheter of claim 20 wherein the proximal arm section is positioned outside of the outer catheter tube when the at least one resilient arm is in the expanded configuration.

24. The ablation catheter of claim 20 wherein the distal arm section is positioned outside of the outer catheter tube when the at least one resilient arm is in the expanded configuration.

25. The ablation catheter of claim 20 wherein the proximal arm section is positioned inside of the outer catheter tube when the at least one resilient arm is in the delivery configuration.

26. The ablation catheter of claim 20 wherein the distal arm section is positioned inside of the outer catheter tube when the at least one resilient arm is in the delivery configuration.

27. A method of treating atrial fibrillation comprising:
inserting an ablation catheter defining a major axis into the left atrium of the heart of a patient;
expanding a resilient arm of the ablation catheter by bending the resilient arm at a bend section in the resilient arm, wherein the resilient arm comprises proximal and distal arm sections extending from the bend section, the distal arm section defining a substantially linear configuration substantially orthogonal to the major axis when the resilient arm is substantially expanded, and the proximal arm section of the at least one resilient arm defining shape selected from the group consisting of cordate, hastate, and sagittate when the resilient arm is substantially expanded;
pulling the proximal arm section of the resilient arm into contact with septal wall tissue; and
passing energy through at least one electrode disposed on the proximal arm section to ablate the septal wall tissue.

28. The method of claim 27 further comprising sensing electrical signals of the septal wall tissue through the at least one electrode disposed on the proximal arm section.

29. The method of claim 28 further comprising repeating the passing energy and sensing steps on another area of septal wall tissue.

30. The method of claim 28 further comprising determining if the proximal arm section is disposed over an arrhythmogenic focus in the left atrium.

31. The method of claim 27 wherein the step of expanding the resilient arm further comprises bending the resilient arm until the proximal arm section extends generally along a lateral axis of the ablation catheter.

32. The method of claim 27 wherein the step of expanding the resilient arm further comprises bending the resilient arm until the distal arm section extends generally along a lateral axis of the ablation catheter.

33. The method of claim 27 further comprising removing an outer catheter tube from the resilient arm before expanding the resilient arm.

34. The method of claim 27 wherein the expanding step further comprises sliding a pin relative to a longitudinal axis of the ablation catheter.

* * * * *